US006726629B1

United States Patent
Frinking et al.

(10) Patent No.: US 6,726,629 B1
(45) Date of Patent: Apr. 27, 2004

(54) ULTRASOUND CONTRAST IMAGING

(75) Inventors: Peter J. A. Frinking, Geneva (CH); E. Ignacio Cespedes, Folsom, CA (US); Nico de Jong, Krimpen aan den Ijssel (NL)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 09/600,219

(22) PCT Filed: Jan. 15, 1999

(86) PCT No.: PCT/GB99/00144
§ 371 (c)(1),
(2), (4) Date: Oct. 25, 2001

(87) PCT Pub. No.: WO99/35967
PCT Pub. Date: Jul. 22, 1999

(Under 37 CFR 1.47)

(30) Foreign Application Priority Data

Jan. 16, 1998 (GB) .............................. 9800813

(51) Int. Cl.⁷ ................................. A61B 8/14

(52) U.S. Cl. ................... 600/458; 600/437; 600/443

(58) Field of Search ................. 600/437–472

(56) References Cited

U.S. PATENT DOCUMENTS

| 3,640,271 A | 2/1972 | Horton |
| 4,483,345 A | 11/1984 | Miwa |
| 5,040,537 A | 8/1991 | Katakura |
| 5,141,738 A | 8/1992 | Rasor et al. |
| 5,255,683 A | 10/1993 | Monaghan |
| 5,410,516 A | 4/1995 | Uhlendorf et al. |
| 5,425,366 A | 6/1995 | Reinhardt et al. |
| 5,456,257 A | 10/1995 | Johnson et al. |
| 5,501,863 A | 3/1996 | Rössling et al. |
| 5,526,816 A | * 6/1996 | Arditi .................. 600/458 |
| 5,540,909 A | 7/1996 | Schutt |
| 5,577,505 A | 11/1996 | Brock-Fisher et al. |
| 5,601,085 A | 2/1997 | Ostensen et al. |
| 5,678,553 A | 10/1997 | Uhlendorf et al. |
| 5,735,281 A | 4/1998 | Rafter et al. |
| 5,749,364 A | 5/1998 | Sliwa et al. |
| 5,833,613 A | * 11/1998 | Averkiou et al. ........ 600/440 |
| 5,833,615 A | * 11/1998 | Wu et al. ............... 600/458 |
| 5,938,612 A | * 8/1999 | Kline-Schoder et al. .... 600/459 |
| 6,117,082 A | * 9/2000 | Bradley et al. .......... 600/447 |
| 6,371,914 B1 | * 4/2002 | Arditi .................. 600/443 |

FOREIGN PATENT DOCUMENTS

| DE | 2946662 | 5/1981 |
| DE | 3637926 C1 | 11/1987 |
| EP | 0 131 540 A2 | 7/1984 |
| EP | 0 322 350 A1 | 12/1988 |
| EP | 0 644 777 B1 | 6/1993 |
| EP | 0 398 935 B1 | 8/1994 |
| EP | 0 717 617 B1 | 8/1994 |
| WO | WO 89/05160 | 6/1989 |
| WO | WO 95/07072 | 3/1995 |
| WO | WO 96/13213 | 5/1996 |

OTHER PUBLICATIONS

D. L. Miller, *Ultrasonic Detection of Resonant Cavitation Bubbles In a Flow Tube By Their Second–Harmonic Emission*; Sep. 1981; pp. 217–224.

Nico de Jong, *A Computerized System that Uses High–Frequency Data for Analysis of Myocardial Contrast Echocardiograms*; Mar. 1990; pp. 99–105.

(List continued on next page.)

*Primary Examiner*—Dennis Ruhl
*Assistant Examiner*—William C. Jung

(57) ABSTRACT

An ultrasound image is obtained by subjecting an object containing an ultrasound contrast enhancement agent to a first imaging pulse burst and then to a second release pulse and then to a second imaging pulse to obtain two images and then comparing the two images to obtain an enhanced image.

14 Claims, 4 Drawing Sheets

OTHER PUBLICATIONS

Ayache Bouakaz; *Noninvasive Measurement of the Hydrostatic Pressure in A Fluid–Filled Cavity Based on the Disappearance Time of Micrometer–Sized Free Gas Bubbles*; 1999; pp. 1407–1415.

Peter J.A. Frinking and Nico de Jong; Modeling of Ultrasound Contrast Agent; IEEE Ultrasonics Symposium; Modeling of Ultrasound Contrast Agents; 1997; pp. 1601–1604.

Albrecht Bauer, Marianne Mahler, Albrecht Urbank, Michael Zomack, Reinhard Schlief & Hans–Peter Niendorf; Microvascular Imaging—Results From A Phase I Study of The Novel Polymeric Ultrasound Contrast Agent; Advances in Echo Imaging Using Contrast Enhancement, Second Ed. 1997; pp. 685–690.

Jeffry E. Powers, Peter N. Burns & Jacques Souquet; Imaging Instrumentation for Ultrasound Contrast Agents;—Advances in Echo Imaging Using Contrast Enhancement, Second Ed. 1997; pp. 139–170.

Volkmar Uhlendorf and Christian Hoffmann; Nonlinear Acoustical Response of Coated Microbubbles in Diagnostic Ultrasound—1994 Ultrasonics Symposium 1559–1562.

Albrecht Bauer, Reinhard Schlief, Michael Zomack, Albrecht Urbank & Hans–Peter Niendorf; Acoustically Stimulated Microbubbles in Diagnostic Ultrasound; Properties and Implications for Diagnostic Use—Advances in Echo Imaging Using Contrast Enhancement, Second Ed.; 1997— pp. 669–684.

Navin C. Nanda & Joel S. Raichlen—Contrast Echocardiography Today; Advances in Echo Imaging Using Contrast Enhancement, Second Edition, 1997; pp. 209–216.

IEEE Engineering In Medicine and Biology; Improvements in Ultrasound Contrast Agents; Nov./Dec. 1996; pp. 72–82.

Volkmar Uhlendorf and Christian Hoffman; Nonlinear Acoustical Response of Coated Microbubbles in Diagnostic Ultrasound; 1994 Ultrasonic Symposium; pp. 1559–1562.

N. de Jong; F.J. Ten Cate, C.T. Lancee; J.R.T.C. Roelandt and N. Bom; Principles and Recent Developments in Ultrasound Contrast Agents; Ultrasonics, vol. 29, Jul. 1991.

N. de Jong; L. Hoff; T. Skotland and N. Bom; Absorption and Scatter of Encapsulated Gas Filled Microspheres; Theoretical Considerations and Some Measurements; Ultrasonics, vol. 30, No. 2; 1992; pp. 95–103.

N. de Jong and L. Hoff; Ultrasound Scattering Properties of Albunex Microspheres; Ultrasonics, vol. 31, No. 3. 1993; pp. 175–181.

N. Sponheim; L. Hoff, A. Waaler, B. Muan; S. Holm, M. Myrum; N. de Jong; and T. Skotland; Albunex—A New Ultrasound Contrast Agent; pp. 103–108.

Nico de Jong, Folkert J. Ten Cate; New Ultrasound Contrast Agents and Technological Innovations; Ultrasonics 34 (1996); pp. 587–590.

A. Bouakaz; N. de Jong; L. Gerfault; C. Cachard; In Vitro Standard Acoustic Parameters of Ultrasound Contrast Agents; Definitions and Calculations; IEEE Ultrasonics Symposium; 1996; pp. 1445–1448.

N. de Jong; Peter Frinking; Folkert ten Cate and Pol van der Wouw; Characteristics of Contrast Agents and 2d Imaging; IEEE Ultrasonics Symposium; 1996; pp. 1449–1458.

Ayache Bouakaz; Nico de Jong; Christian Cachard; Standard Properties of Ultrasound Contrast Agents; Ultrasound in Med. & Biol. vol. 24, No. 3. 1998; pp. 469–472.

Peter J.A. Frinking; Ayache Bouakaz; Nico de Jong; Folkert J. Ten Cate; Siobhan Keating; Effect of Ultrasound On the Release of Micro–Encapsulated Drugs; Ultrasonics 36 (1998); pp. 709–712.

Peter J.A. Frinking and Nico de Jong; Acoustic Modeling of Shell–Encapsulated Gas Bubbles; Ultrasound in Med. & Biol. vol. 24; No. 4, 1998; pp. 523–533.

Nico de Jong; Improvements in Ultrasound Contrast Agents; IEEE Engineering In Medicine and Biology; Nov./Dec. 1996; pp. 72–73.

First European Symp. On Ultrasound Contrast Imaging, Abstract Book, Cate and deJong, Jan. 25–26, 1996.

* cited by examiner

ULTRASOUND CONTRAST IMAGING

The present invention relates to ultrasound imaging and more particularly to an improved multipulse and enhancement strategy for ultrasound imaging of an object containing an ultrasound contrast enhancement imaging agent.

Ultrasound contrast agents can be introduced into the body to reflect or absorb ultrasound energy, or to resonate when exposed to such energy, and thereby provide an enhanced image of a part of the body. Examples of such contrast agents, in the form of hollow microcapsules, are given in Japanese patent applications nos. 508032/1992 and 509745/1994 and in PCT/GB95/02673 (WO 96/15814). Such agents are injected into the patient's bloodstream and then the patient is subjected to ultrasound radiation.

In the present invention the ultrasound sequence comprises a multiple sequence comprising a first pulse burst at a first frequency and low amplitude followed by a second pulse burst at second frequency and relatively higher amplitude. This second pulse is of sufficient magnitude to induce power enhanced scattering, as defined, in a region of interest. This is then further followed by a third pulse burst of a third frequency and lower amplitude.

Power enhanced scattering is defined as providing an acoustic pulse at an amplitude at least sufficient to cause a change in the acoustic properties of the region of interest to, for example, cause bubbles to be released from the microcapsules.

The present invention provides a method of producing an ultrasound image of an object containing an ultrasonic contrast imaging agent comprising subjecting the object to a first pulse burst of a first frequency and first power, subjecting the object to a second pulse burst of a second frequency in combination with a second power for optimal bubble release and subjecting the object to a third pulse burst of a third frequency and third power, obtaining a first image of the object as a result of the first pulse burst, obtaining a second image of the object as a result of the third pulse burst and comparing the first and second images to obtain a final enhanced image.

Preferably said first power is a low power relative to said second power which is a high power and said third power is a low power relative to said second power.

Preferably in a first embodiment the first and third pulse bursts are at a frequency higher than that of the second pulse bursts.

Alternatively the first and third pulse burst are at a frequency lower than that of the second pulse burst.

Preferably the first and third pulse bursts are identical or have a defined and known relationship.

Preferably the first and third pulse bursts comprise a relatively lower number of cycles than the second pulse burst.

In a specific embodiment the first and third pulse bursts comprise a single cycle.

Preferably the second pulse burst comprises a plurality of cycles. In a specific embodiment this comprises four or more cycles.

Preferably the time between the first and third pulse bursts is less than 100 $\mu s$.

In a specific embodiment the third pulse burst can be combined with or overlap with the second pulse bursts. Any image pulse obtained from the third pulse burst can be filtered out from any interference from the second pulse bursts by virtue of the difference in frequencies.

In the imaging method a first image is obtained during the first pulse burst and a second image is obtained during the third pulse burst. The second higher amplitude pulse burst comprises a release burst for release of bubbles from a suitable agent such as Quantison.

The invention also provides apparatus for carrying out the above method.

Suitable microcapsules include those disclosed as "QUANTISON"™ microcapsules by Andaris Limited, and described in WO92/18164 (U.S. Pat. No. 5,518,709), WO94/08627 and WO96/15814 (U.S. Ser. No. 08/676,344 filed Jul. 19, 1996), all of which are incorporated herein by reference. The microcapsules are made by spray-drying a solution of serum albumin to form hollow microcapsules generally of diameter 1 to 10 $\mu m$; for example 90% may have a diameter of 1.0 to 9.0 $\mu m$ or 1 to 6.0 $\mu m$, as measured in a Coulter Counter Multmizer II. However, any gas containing microcapsule, microsphere or microparticle which releases the gas on irradiation with a non-physiologically harmful dose of ultrasound may be used in the methods of the invention.

In an enhancement sequence the first and second images obtained during the first and third pulse bursts are compared with each other to provide a combined improved image, for example by subtractive decorrelation.

Embodiments of the present invention will now be described with reference to the accompanying drawings in which.

Figure 1:
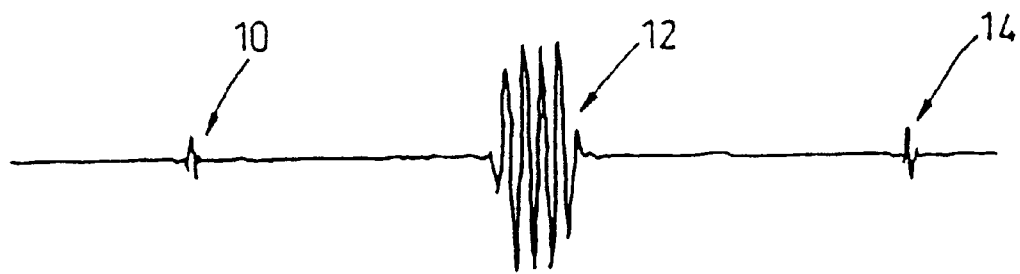
FIG. 1 shows an exemplary pulse burst sequence according to the present invention.

With reference to FIG. 1, an exemplary multipulse sequence comprises a first pulse burst 10 at relatively low amplitude and a third pulse burst 14 also at relatively low amplitude, both pulse bursts being at relatively high frequency, e.g 5 MHz and relatively fewer cycles compared to the second pulse burst. The preferred embodiment comprises a pulse that is shaped for maximum resolution on imaging. In the specific embodiment shown only one cycle is used.

The first and third pulse bursts are preferably identical but they may have a defined relationship and in this case the processing circuitry will compensate to provide a comparative image.

In between these pulse bursts is positioned a second pulse burst having a power selected for optimal bubble release. In the preferred embodiment shown the second pulse burst is a relatively low frequency (e.g. 2 MHz) pulse burst having a greater amplitude. The second pulse burst also preferably has a greater number of cycles than the first pulse burst. Preferably the second pulse burst comprises a pulse burst that is optimal for gas bubble release. In a specific embodiment the pulse burst has four or more cycles.

The second pulse burst could, however, be of higher frequency, in which case the power (amplitude) of the second pulse burst could for some microcapsules be lower. What is required is a pulse burst of such frequency and power for the microcapsules that bubble release occurs and this will depend on a number of factors, including the type of microcapsule, which factors will be known to the person skilled in the art.

In operation two images are taken, one on each of the first and third pulse bursts, and the second pulse burst is used to induce Power Enhanced Scattering (PES) of bubbles from microcapsules contained in the region of interest. The image taken during the first pulse burst is compared with that in the third pulse burst to obtain an enhanced comparative image.

Figure 2:
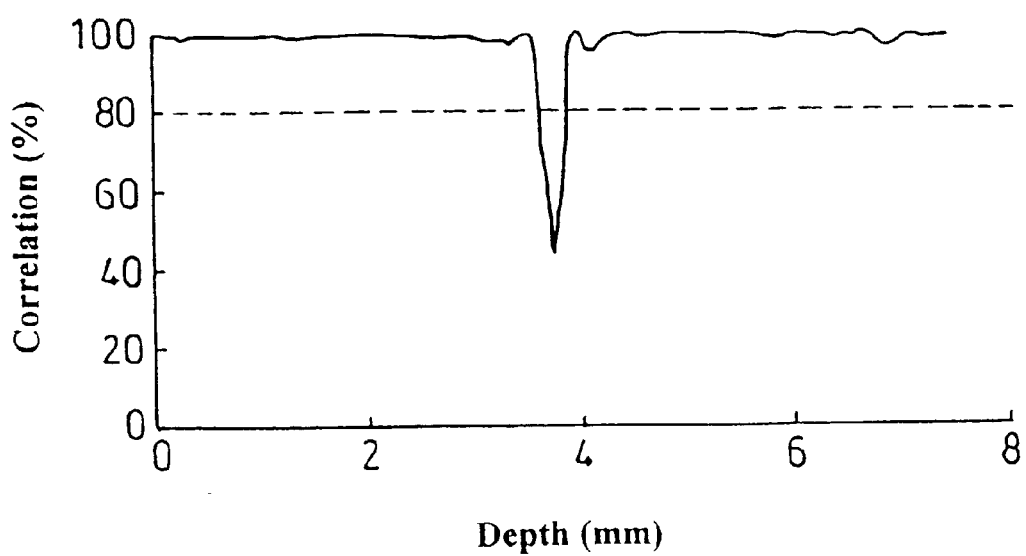
FIG. 2 shows a decorrelation profile obtained using the pulse burst sequence of FIG. 1.

FIG. 2 shows the comparison, in this case a subtractive decorrelation obtained from the pulse sequence of FIG. 1 with thresholding of the data (from FIGS. 3 and 4) using an 80% correlation level. This clearly shows the detection of a single fibre of 200 μm, in diameter at a depth of 75 mm when the fibre is filled with QUANTISON. The experiment is set up to simulate a triggered M-mode with the test object being a single fibre containing QUANTISON.

Figure 3:
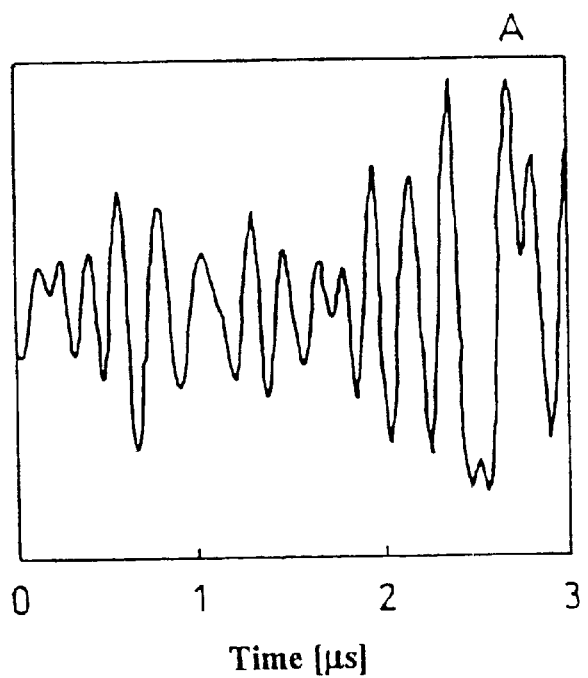
FIG. 3 shows an image resulting from an experiment with the first and third pulses without the power enhanced scattering effect produced by the second pulse.

FIG. 3 represents the result of the two Radio-Frequency (RF) imaging pulses without the high amplitude burst, in which no PES and no free air bubbles are detected.

Figure 4:
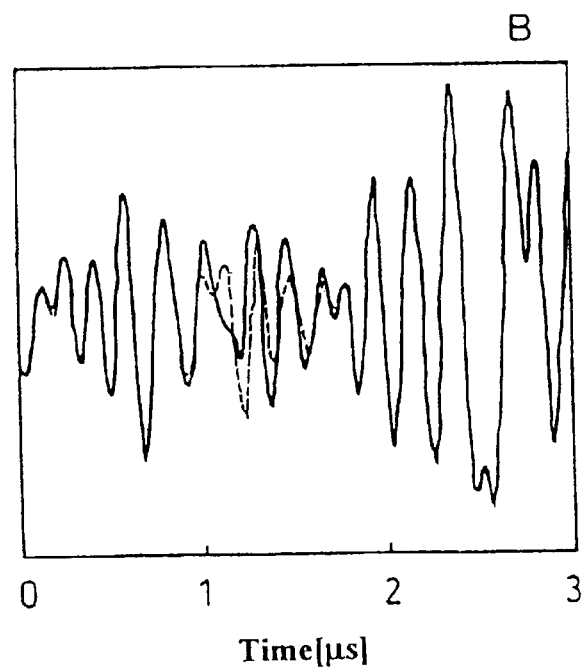
FIG. 4 shows the images resulting when all three pulses are present and with FIG. 2 shows the advantages of decorrelation.

FIG. 4 shows the result when the second burst, in between the two image pulses, is switched on.

In this case, the second imaging pulse (the third pulse burst) detects the generated free air bubbles. The change in amplitude is minimal, due to the high scattering surrounding material However, in combination with the 'comparison-based strategy', these minimal changes can be accurately detected.

The complete pulse sequence should be carried out within as short a period of time as is reasonably practical, bearing in mind the persistence of the evoked bubble release, acoustic velocities and depth of region of interest. In a particular example for the pulse sequence of FIG. 1, the total time period is 100 μs.

Other frequencies can be used for the first/third and the second pulse. For example, the first/third pulses can be 3 Mhz and the second 500 khz or the first/third pulses can be 5 MHz and the second 1 MHz.

The power of the first (10) and third (14) pulse bursts should be such as not to induce any power enhanced scattering (release of bubbles) from the QUANTISON. Thus the power of the first and third pulses should preferably not be higher than 0.1 MPa The power of the centre (second) pulse burst must be such as to produce power enhanced scattering as defined, and should preferably be above 0.6 MPa for QUANTISON.

The powers however could vary for other agents.

Because the frequency of the second pulse burst 12 is different from that of the first/third pulse bursts, it is convenient to filter out any residual effects from the second pulse burst when imaging.

This enables the third pulse burst to follow quickly on after or even overlap the second but as stated above, it is generally considered that the total sequence time, which should be as short as possible, will have to be a minimum of 100 μs for an object depth of 75 mm for most practical purposes. The total time could possibly be shorter if the imaged object was at a shallower depth.

Figure 5:
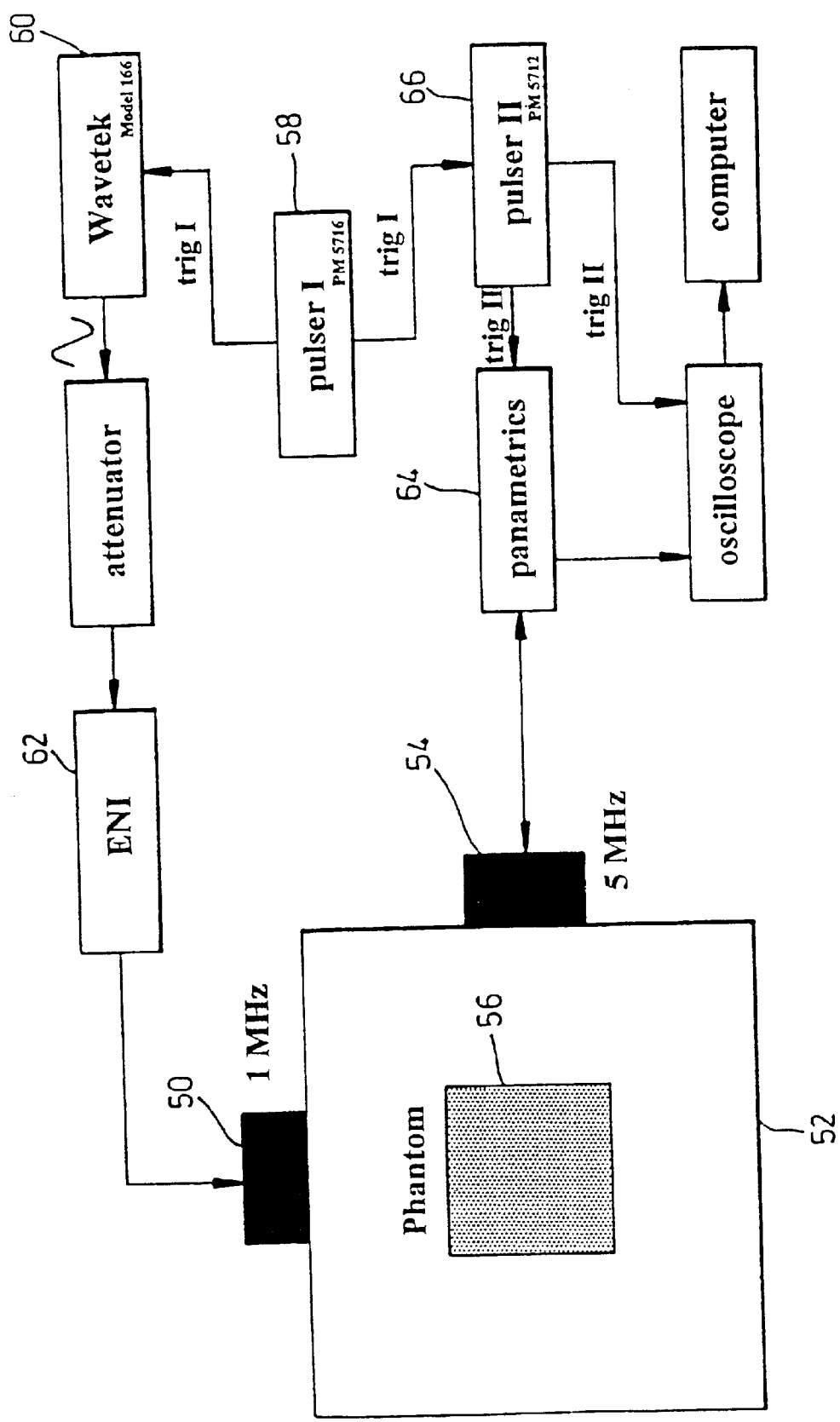
FIG. 5 shows a block diagram of apparatus suitable for the present invention and FIG. 6 shows a transducer for use with the present invention.

Apparatus suitable for the invention is illustrated in FIG. 5.

A 1 MHz single element transducer 50 (Panametrics, Waltham, Mass., USA) with a focus at 7.5 cm is mounted in water bath 52 filled with Isoton® II (Coulter Diagnostics) and used as the high power transmitter. Perpendicular to the acoustical beam of this transducer a 5 MHz single element broadband transducer 54 (Panametrics, Waltham, Mass., USA), with a focus at 7.5 cm, is mounted and used to probe the target 56 positioned in the center of the waterbath (transmit/receive). The 1 MHz high power sinusoidal signal of 10 cycles with a peak-peak acoustical pressure of 1.8 MPa and repetition rate of 1 Hz is generated by a pulse generator 58 (PM5716, Philips), a Wavetek signal generator 60 and a linear power amplifier 62 model A-500 (ENI, N.Y.). A short 5 MHz pulse is generated and received by a pulser/receiver 64 (5052 PR, Panametrics, Waltham, Mass., USA). The received signal can be amplified from +40dB to −40 dB in steps of 2 dB. The amplified signal is filtered with low pass Cheychev filer and digitized by a Lecroy 9400A (Lecroy, Chestnut Ridge, N.Y., USA) digital oscilloscope (100 MHz, 8 bits). The pulser/receiver is synchronized by a pulse generator 66 (PM 5712, Philips) with a delay of 0.5 ms relative to the 1 MHz transmitted signal. The output signals are recorded over time windows of 10 μs and transferred to a personal computer (Compaq 386/20e) for further analysis.

In an alternative embodiment the third pulse 12 could be combined within the second pulse since the scattered signal from the third pulse can be filtered out.

This will provide a shorter time period for the total experiment.

For other uses, for example for velocity measurement, it is possible for the first and third pulses to be of relatively low frequency and for the second pulse to be of relatively higher frequency, i.e. the opposite of the first example.

Figure 6:
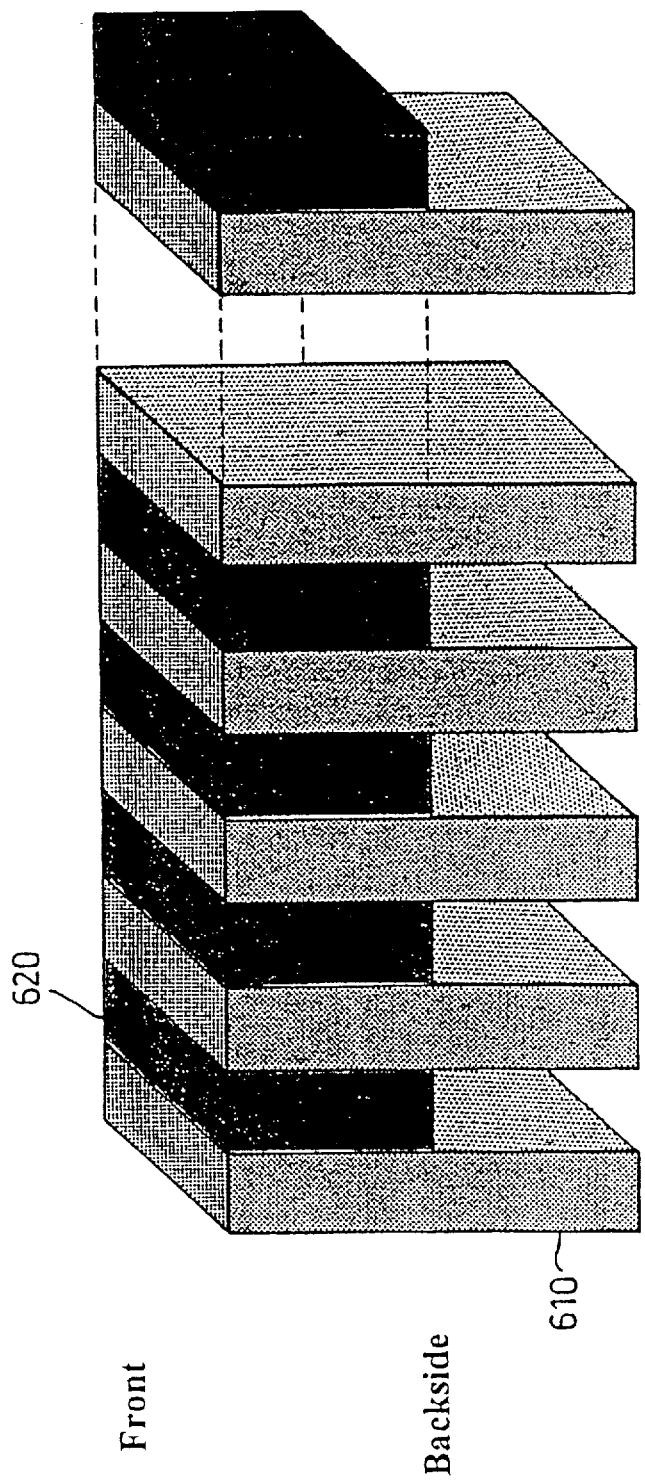
Figure 6:

With reference now to FIG. 6, a design of a transducer 600 with a frequency response suitable for the present invention is shown.

In this design two separate transducer elements 610, 620 are used. The first transducer element 610 is sensitive to low frequency and the second 620 is sensitive to high frequency. Both elements may be of the piezoelectric type.

The low frequency transducer (type 610) is used for sending, the other one 620 can be used for both receiving alone and for transmitting and receiving for imaging. For array transducers the two transducer types (610, 620) can be merged as shown by interleaving the two types, thereby defining the e.g. the odd elements as type 1 and the even elements as type 2. Other distributions are also possible. Type 2 transducer can be used for imaging in both the fundamental as well as the second harmonic mode.

What is claimed is:

1. A method of producing an ultrasound image of an object containing an ultrasonic contrast imaging agent comprising:
   (a) subjecting the object to a first pulse burst of a first frequency and first power;
   (b) subjecting the object to a second pulse burst of a second frequency in combination with a second power;
   (c) subjecting the object to a third pulse burst of a third frequency and third power;
   (d) obtaining a first image of the object as a result of the first pulse burst;
   (e) obtaining a second image of the object as a result of the third pulse burst;
   (f) comparing the first and second images; and
   (g) obtaining a final enhanced image as a function of (f).

2. A method of producing an ultrasound image as claimed in claim 1 in which said first power is a low power relative to said second power which is a high power and said third power is a low power relative to said second power.

3. A method as claimed in claim 1 in which the first pulse burst is of relatively high frequency, the second pulse burst is of relatively low frequency and the third pulse burst is of relatively high frequency.

4. A method as claimed in claim 1 in which the first pulse burst is of relatively low frequency, the second pulse burst is of relatively high frequency and the third pulse burst is of relatively low frequency.

5. A method as claimed in claim 1 in which the first and third pulse bursts are identical.

6. A method as claimed in claim 1 in which the first and third pulse bursts comprise a relatively lower number of cycles than the second pulse burst.

7. A method as claimed in claim 6 in which the first and third pulse bursts comprise a single cycle.

8. A method as claimed in claim 1 in which the second pulse burst comprises a plurality of cycles.

9. A method as claimed in claim 8 in which the second pulse burst comprises four or more cycles.

10. A method as claimed in claim 1 in which the time between the first and third pulse bursts is less than 100 $\mu$s.

11. A method as claimed in claim 1 in which the second higher amplitude pulse burst comprises a release burst for release of bubbles from the contrast imaging agent.

12. Apparatus for producing an ultrasound image of an object containing an ultrasonic contrast imaging agent including first transmitter means for subjecting the object to a first pulse burst of a first frequency and first power, second transmitter means for subjecting the object to a second pulse burst of a second frequency in combination with a second power for optimal bubble release and third transmitter means for subjecting the object to a third pulse burst of a third frequency and third power, receiver means for obtaining a first image of the object as a result of the first pulse burst, receiver means for obtaining a second image of the object as a result of the third pulse burst and processing means for comparing the first and second images to obtain a final enhanced image.

13. Apparatus as claimed in claim 12 in which said outputs of said transmitter means are such that first power is a low power relative to said second power which is a high power and said third power is a low power relative to said second power.

14. Apparatus as claimed in claim 12 including a transducer for emitting and receiving low and high frequency acoustic signals said transducer comprising a plurality of first and second types of transducer elements, said first and second elements being positioned adjacent to each other to form an interleaved transducer array.

* * * * *